(12) United States Patent
Zemlok et al.

(10) Patent No.: US 10,213,266 B2
(45) Date of Patent: Feb. 26, 2019

(54) ROBOTIC SURGICAL ASSEMBLIES AND ADAPTER ASSEMBLIES THEREOF

(71) Applicant: Covidien LP, Mansfield, MA (US)

(72) Inventors: Michael Zemlok, Prospect, CT (US);
Chi Min Seow, New Haven, CT (US);
Jaimeen Kapadia, Boston, MA (US);
Richard Lech, Hamden, CT (US);
Mark MacLeod, Southbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/887,391

(22) Filed: Feb. 2, 2018

(65) Prior Publication Data

US 2018/0153634 A1 Jun. 7, 2018

Related U.S. Application Data

(63) Continuation-in-part of application No. 15/116,903, filed as application No. PCT/US2015/014542 on Feb. 5, 2015, now Pat. No. 9,987,094.

(Continued)

(51) Int. Cl.
*H02P 6/04* (2016.01)
*A61B 34/00* (2016.01)
(Continued)

(52) U.S. Cl.
CPC .............. *A61B 34/76* (2016.02); *A61B 34/30* (2016.02); *A61B 34/71* (2016.02); *G01L 3/108* (2013.01); *A61B 2017/00477* (2013.01)

(58) Field of Classification Search
CPC .......... G05B 2219/41378; G05B 17/00; A61B 34/30; A61B 34/71; A61B 34/76;
(Continued)

(56) References Cited

U.S. PATENT DOCUMENTS

| 4,384,493 A | * | 5/1983 | Grunbaum | ........... G01R 31/343 |
| | | | | 73/862.29 |
| 5,327,790 A | * | 7/1994 | Levin | ........................ B25J 9/12 |
| | | | | 73/862.321 |

(Continued)

FOREIGN PATENT DOCUMENTS

| CN | 102401709 A | 4/2012 |
| EP | 0656500 A1 | 6/1995 |

(Continued)

OTHER PUBLICATIONS

Chinese Office Action dated May 28, 2018 issued in CN Appln. No. 2015800075513.

(Continued)

*Primary Examiner* — Antony M Paul

(57) ABSTRACT

A torque transducer for mounting a motor includes a mounting flange, a motor flange, a body, and a strain gauge. The mounting flange is configured to secure the torque transducer to a fixed structure. The motor flange is configured to secure to a motor. The body interconnects the mounting and motor flanges. The body defines a channel about a longitudinal axis of the body and is configured to flex in response to the mounting flange and the motor flange rotating relative to one another in response to torque of the motor. The strain gauge is positioned on the body to measure flexation of the body.

12 Claims, 10 Drawing Sheets

Related U.S. Application Data

(60) Provisional application No. 61/987,893, filed on May 2, 2014, provisional application No. 61/937,044, filed on Feb. 7, 2014.

(51) Int. Cl.
*A61B 34/30* (2016.01)
*G01L 3/10* (2006.01)
*A61B 17/00* (2006.01)

(58) Field of Classification Search
CPC .......... A61B 2017/00477; G01L 3/108; H02P 29/00; H02P 1/00; H02P 3/00; H02P 6/00; H02P 21/00; H02P 41/00; H02P 6/04; H02P 6/08; H02K 7/14; B25J 19/02
USPC ...... 318/568.12, 568.16, 568.2, 400.14, 432, 318/400.01, 400.15, 700, 727, 799; 901/8, 10, 19, 23, 30
See application file for complete search history.

(56) References Cited

U.S. PATENT DOCUMENTS

| | | | |
|---|---|---|---|
| 5,792,135 A | 8/1998 | Madhani et al. | |
| 7,395,724 B2* | 7/2008 | Bunyer | G01L 3/10 73/862.338 |
| 8,161,827 B2* | 4/2012 | Kato | G01L 3/1457 73/862.044 |
| 8,425,436 B2* | 4/2013 | Sankai | A61H 1/0237 318/400.39 |
| 2007/0129846 A1 | 6/2007 | Birkenbach et al. | |
| 2010/0005907 A1 | 1/2010 | Kato et al. | |
| 2012/0048628 A1* | 3/2012 | Kawanami | B25J 9/0003 180/21 |
| 2012/0116416 A1 | 5/2012 | Neff et al. | |

FOREIGN PATENT DOCUMENTS

| | | |
|---|---|---|
| JP | 55006268 | 1/1980 |
| JP | 2003083824 A | 3/2003 |
| JP | 2009058388 A | 3/2009 |
| JP | 2012047460 A | 3/2012 |
| WO | 2012165068 A1 | 12/2012 |

OTHER PUBLICATIONS

European Search Report dated Oct. 30, 2017, issued in EP Appln. No. 15746311.
Japanese Office Action dated Oct. 15, 2018, issued in JP Appln. No. 2016544516.
Australian Office Action dated Nov. 1, 2018, issued in AU Appln. No. 2015214157.

* cited by examiner

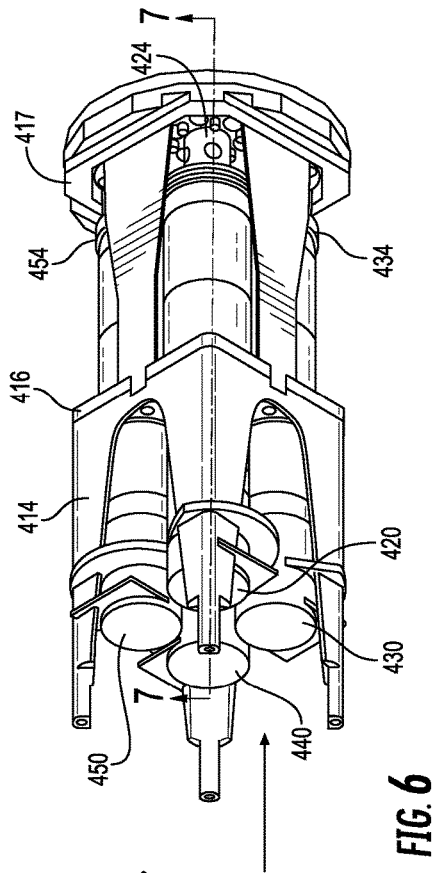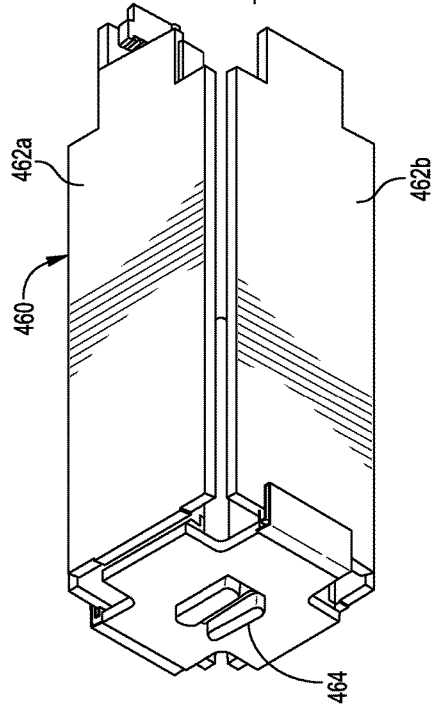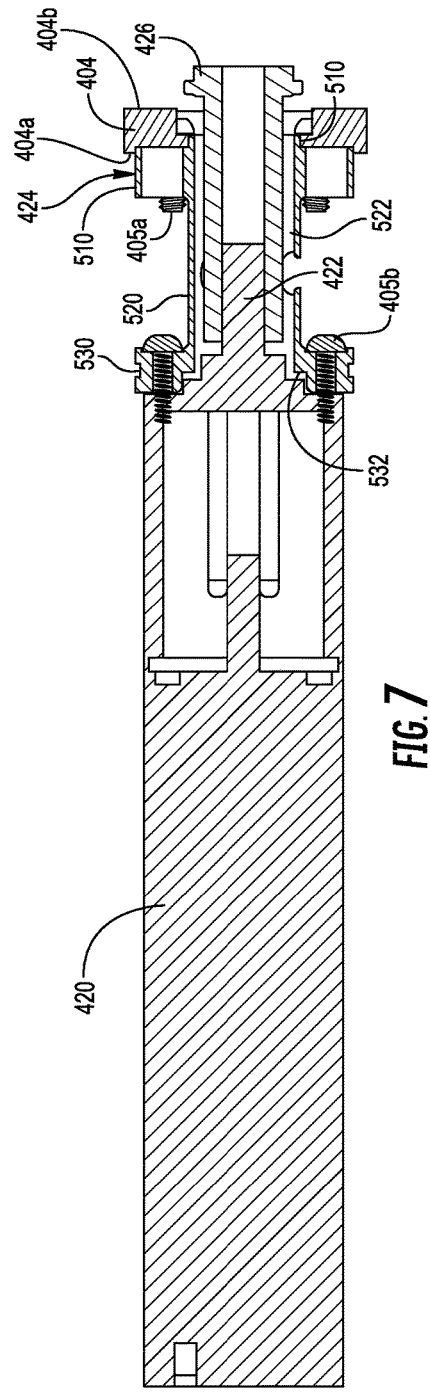
FIG. 6
FIG. 7

ROBOTIC SURGICAL ASSEMBLIES AND ADAPTER ASSEMBLIES THEREOF

CROSS-REFERENCE TO RELATED APPLICATIONS

This application is a continuation-in-part of U.S. patent application Ser. No. 15/116,903, filed Aug. 5, 2016, which claims the benefit of, and priority to, International Application PCT/US2015/014542, filed Feb. 5, 2015, which claims benefit of, and priority to, U.S. Provisional Patent Application Ser. Nos. 61/987,893, filed May 2, 2014, and 61/937,044, filed Feb. 7, 2014. The entire contents of each of the above applications are hereby incorporated by reference.

BACKGROUND

Robotic surgical systems have been used in minimally invasive medical procedures. During such a medical procedure, the robotic surgical system is controlled by a surgeon interfacing with a user interface. The user interface allows the surgeon to manipulate an end effector that acts on a patient. The user interface includes an input controller or handle that is moveable by the surgeon to control the robotic surgical system.

The end effectors of the robotic surgical system are positioned at the end of robotic arms. Each end effector is manipulated by an instrument drive unit (IDU). The IDU includes a drive motor that is associated with the end effector to move the end effector about a respective axis or to perform a particular function of the end effector (e.g., approximate, pivot, etc. jaws of the end effector). The IDU can include a plurality of drive motors with each drive motor being associated with a respective degree of freedom or function of the end effector.

Each drive motor of the IDU can be associated with the respective degree or degrees of freedom of the end effector by a drive mechanism (e.g., a drive cable, a drive rod and/or a drive screw). To precisely control the end effector about the degree(s) of freedom the respective drive mechanism can be pretensioned.

There is a continuing need to pretension and limit forces experienced by the drive cables. In addition, there is a continuing need for precisely and accurately measuring the force applied by the drive motors in order to anticipate and predict a life expectancy of the drive motors and drive mechanisms.

SUMMARY

This disclosure relates generally to torque transducers that precisely and accurately measure force applied by drive motors. The torque transducers can measure torque when the drive motors are active and inactive such that the torque transducers can measure pretension in the drive cables and can be used to limit forces experienced by the drive cables. It is contemplated that the torque transducers can be used to provide increased fidelity or precision in control of drive motors for surgical devices and feedback in the control of drive motors for the surgical devices including, but not limited to, staplers, wristed or cable controlled devices, energy based devices, harmonic devices, rod actuated devices, graspers, knives, scissors, dissectors, drills, saws (linear or orbital), tacker, hernia anchor and clip devices, and biopsy devices. It is also contemplated that the torque transducers can be part of a sterile interface module (SIM) for driving endoscope rotation, endoscope manipulation, linear drive mechanisms, screw drive mechanism, capstan driven cable tension mechanisms, linear driven cable tension mechanisms, gear driven mechanism, and belt driven mechanisms. It will be appreciated that a SIM maintains a sterile interface while enabling transmission of rotational and/or translational forces and transmission of electrical signals (e.g., power, control, feedback, etc.) between driving mechanisms and driven mechanisms.

The increased fidelity or precision control and feedback may be advantageous for controlling functions of surgical devices including, but not limited to, limiting articulation or position load limits induced or driven by the system; limiting direction overload induced or driven by the system; limiting clamping pressures, load, or direction induced or driven by the system; limiting wristed movements or direction load induced or driven by the system; rotating a device, a device shaft, or an end effector including driving belt driven rotation gear motors; retracting loads to confirm proper function by consistent loading or back drive; recognition of end stops and distal limit positions; limiting drive actuation or load thresholds; firing implantables including staples, tacks, or clips by verifying formation and formation quality; determining dissection or jaw spreading/opening loads; determining collisions through mechanical shock or heavy load biased or thresholds; absence of a reload or an implantable (staple, tack, or clip); activating a knife or cutting mechanism back drive; locking out a device prevent firing in the absence of an implantable; determining stapler length through a force slope increase that corresponds to the device reload length or stroke; back driving torque from a SIM back out device activation that creates additional drag on one or more target drives; setting staple or cutting load limits to prevent damage or firing over undesired tissue, bone, ligament, tubes staple lines, or other devices or implantables; activating harmonic devices; monitoring for undesired vibrations or inconsistent or irregular back drive loads, and calibrating cannulas with instruments and devices. The increased fidelity or precision control and feedback can be used in a variety of configurations to perform a variety of functions including, but not limited to, confirm that a drive is properly coupled by axial loads in a spring loaded SIM coupler; identify a device or approach of a distal limit for a mechanical feature or bump; monitor the degradation of drive efficiency to control or limit device life; limit load spikes to extend device life; provide additional fidelity for haptic reaction forces or vibratory feedback of end user controls; prevent undesired loads on a device or end effector; limit tension in belts and cables to prolong fatigue life; initializing, homing, calibrating, testing, or confirming the type of device for a motor drive current feedback, rotational encoder, linear encoder, linear load sensor, linear switch, or position sensor; monitor vibration or backlash to determine drive coupler wear and degradation; manage end of life by monitoring backlash range, belt tension back drive, or belt tension vibrations; monitor back drive loads induced on the end effector or reload of a device; and monitor end effector loads back driven by the end user or through collisions on applied loads with the patient or other devices to allow feedback to the end user or to stop the system if a load limit is approached or surpassed.

In accordance with an aspect of the present disclosure, a torque transducer for mounting a motor includes a mounting flange, a motor flange, a body, and a strain gauge. The mounting flange is configured to secure the torque transducer to a fixed structure. The motor flange is configured to secure to a motor. The body interconnects the mounting and motor flanges. The body defines a channel about a longitudinal axis of the body and is configured to flex in response to the mounting flange and the motor flange rotating relative to one another in response to torque of the motor. The strain gauge is positioned on the body to measure flexation of the body.

In aspects, the body has a high strain region configured to amplify flexation in response to a given torque. The body may have a low strain region adjacent each of the mounting and motor flanges. The high strain region can be disposed between the low strain regions.

In some aspects, the mounting flange includes a ring that is configured to position the torque transducer relative to a fixed structure. The motor flange may define a recess that is configured to position the torque transducer relative to a motor.

In another aspect of the present disclosure, an instrument drive unit includes a mounting plate, a first motor, and a first torque transducer. The first motor has a drive shaft that extends towards the mounting plate. The first toque transducer includes a motor flange, a mounting flange, a body, and a strain gauge. The motor flange is secured to the first motor and the mounting flange is secured to the mounting plate. The body interconnects the mounting and motor flanges. The body defines a channel about a longitudinal axis of the body. The body is configured to flex in response to the mounting flange and the motor flange rotating relative to one another in response to torque of the first motor. The drive shaft of the first motor extending into the channel. The strain gauge is positioned on the body to calculate toque applied by the first motor from flexation of the body.

In aspects, the first torque transducer is configured to sample torque of the first motor at a rate in a range of about 10 KHz to about 50 KHz. The first torque transducer may be configured to measure torque of the first motor when the first motor is energized and when the first motor is deenergized.

In some aspects, the mounting flange of the first torque transducer includes a ring that is disposed about the channel. The ring can extend towards the mounting plate such that the mounting plate receives the ring to position the first torque transducer relative to the mounting plate. The motor flange can define a recess about the channel. The first motor can be received in the recess to position the first motor relative to the first toque transducer.

In certain aspects, the instrument drive unit has a motor assembly that includes the first motor, a second motor that is secured to the mounting flange by a second torque transducer, a third motor that is secured to the mounting flange by a third torque transducer, and a fourth motor that is secured to the mounting flange by a fourth torque transducer. The instrument drive unit can include a cage assembly that extends proximally from the mounting flange. The cage assembly is disposed about the motor assembly such that each of the motors of the motor assembly is suspended within the motor assembly by a respective one of the torque transducer such that rotation of each of the motors about a respective longitudinal motor axis is unrestrained except for by a respective one of the torque transducers.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIG. 6 is a partially assembled view of components of the instrument drive unit of FIG. 5;

FIG. 7 is a cross-sectional view taken along section line 7-7 of FIG. 6;

DETAILED DESCRIPTION

Figure 1:
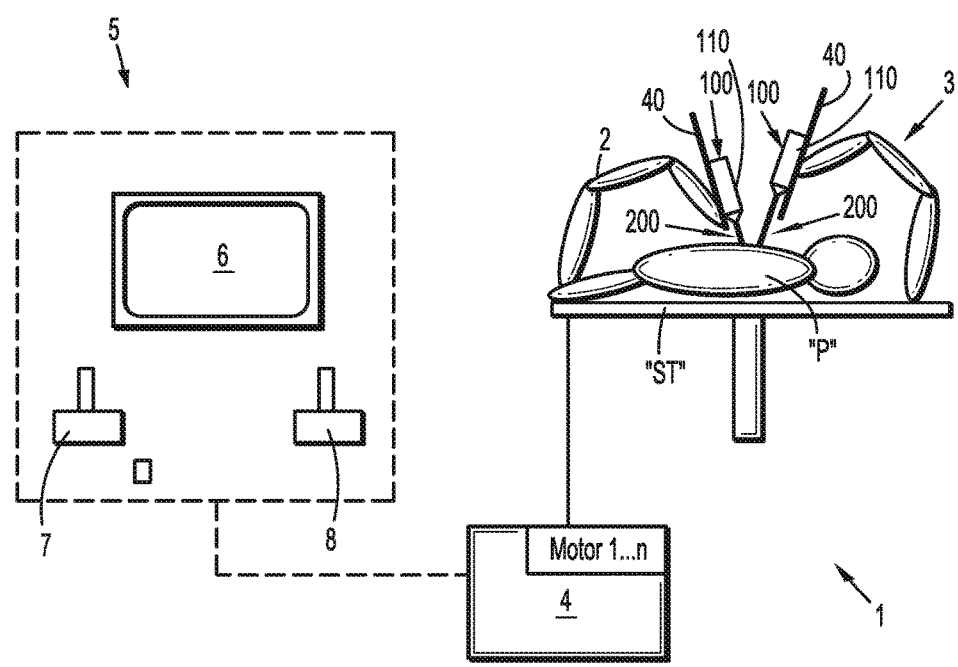
FIG. 1 is a schematic illustration of a robotic surgical system including a robotic surgical assembly in accordance with the present disclosure.

Embodiments of the presently disclosed surgical assembly including a surgical instrument holder, an instrument drive unit (IDU), an adapter assembly, and an endoscope, and methods thereof, are described in detail with reference to the drawings, in which like reference numerals designate identical or corresponding elements in each of the several views. As used herein the term "distal" refers to that portion of the surgical instrument holder, IDU, adapter assembly, and/or endoscope, that is closer to the patient, while the term "proximal" refers to that portion of the surgical instrument holder, IDU, adapter assembly, and/or endoscope, that is farther from the patient.

Referring initially to FIG. 1, a surgical system, such as, for example, a robotic surgical system 1, generally includes a plurality of surgical robotic arms 2, 3 having a robotic surgical assembly 100 including a surgical instrument 200A (FIG. 2A) or, for example, an endoscope 200B (FIG. 2B) removably coupled to a slide rail 40 of surgical robotic arms 2, 3; a control device 4; and an operating console 5 coupled with control device 4.

Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) may be set up to activate the drives, in particular by means of a computer program, in such a way that robotic arms 2, 3, the attached robotic surgical assembly 100, and thus surgical instrument 200A or endoscope 200B execute a desired movement according to a movement defined by means of manual input devices 7, 8. Control device 4 may also be set up in such a way that it regulates the movement of robotic arms 2, 3.

Robotic surgical system 1 is configured for use on a patient "P" lying on a surgical table "ST" to be treated in a minimally invasive manner by means of a surgical instrument 200A or endoscope 200B. Robotic surgical system 1 may also include more than two robotic arms 2, 3, the additional robotic arms likewise being connected to control device 4 and being telemanipulatable by means of operating console 5. A surgical instrument 200A, or, for example, an endoscope 200B, may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control an individual motor 420 (FIG. 2B) of an IDU 400 of robotic surgical assembly 100 that actuates a drive assembly 160 of an adapter assembly 120 to effect rotation of surgical instrument 200A or endoscope 200B. In addition, control device 4 may control the operation of a rotation motor, such as, for example, a canister motor "M" (FIG. 2B) of surgical instrument holder 102, configured to drive a relative rotation of motor assembly 410 of IDU 400 and in turn adapter assembly 120 and endoscope 200, as will be described in detail below. In embodiments, each motor of the IDU 400 can be configured to actuate a drive rod/cable or a lever arm to effect operation and/or movement of an electromechanical surgical instrument 200A.

For a detailed discussion of the construction and operation of a robotic surgical system, reference may be made to U.S. Pat. No. 8,828,023, filed on Nov. 3, 2011, entitled "Medical Workstation," the entire contents of which are incorporated by reference herein.

Figure 2A:
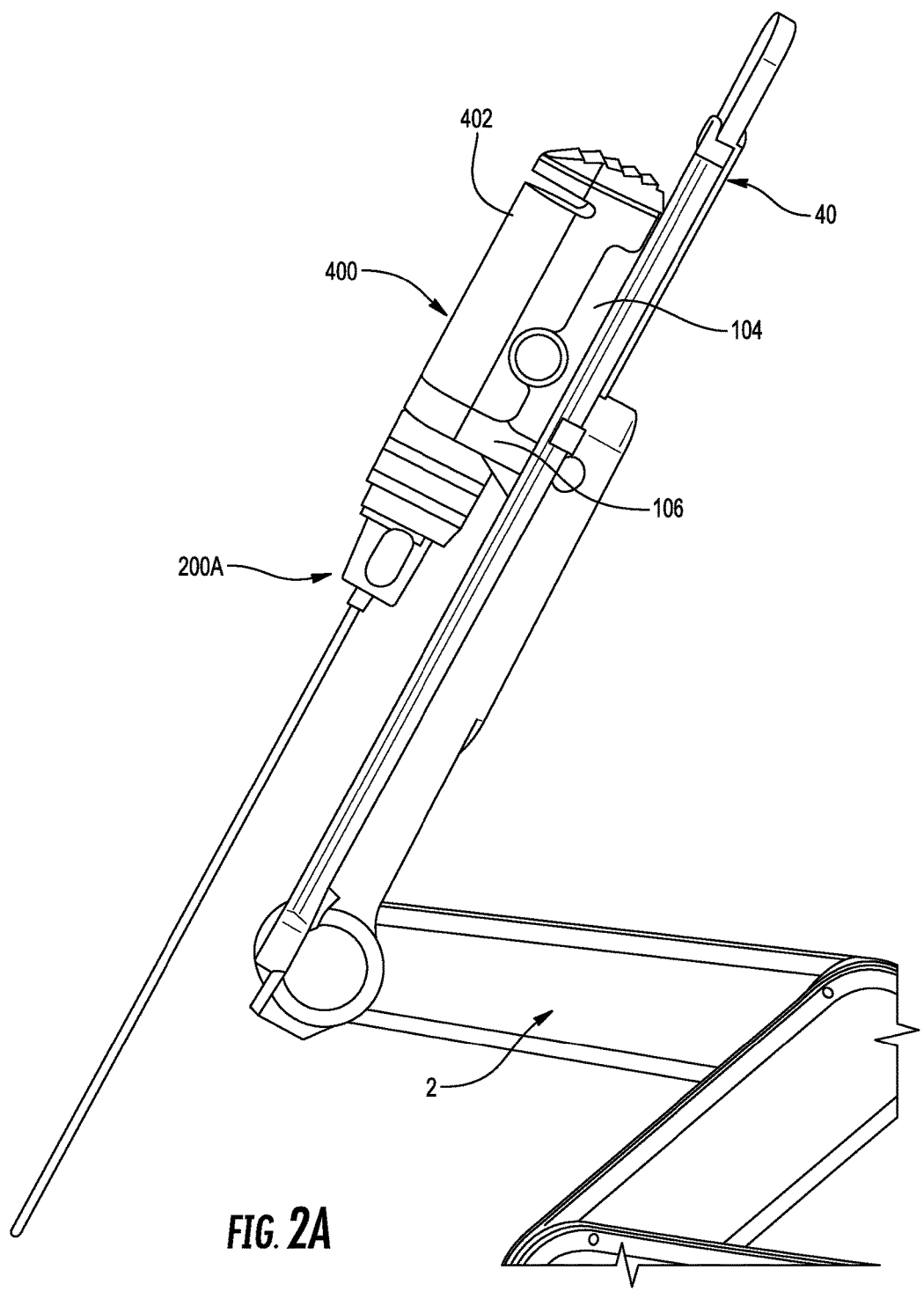
FIG. 2A is a side, perspective view of the surgical assembly of FIG. 1 including a surgical instrument holder, an IDU, an adapter assembly, and a surgical instrument.
Figure 2B:
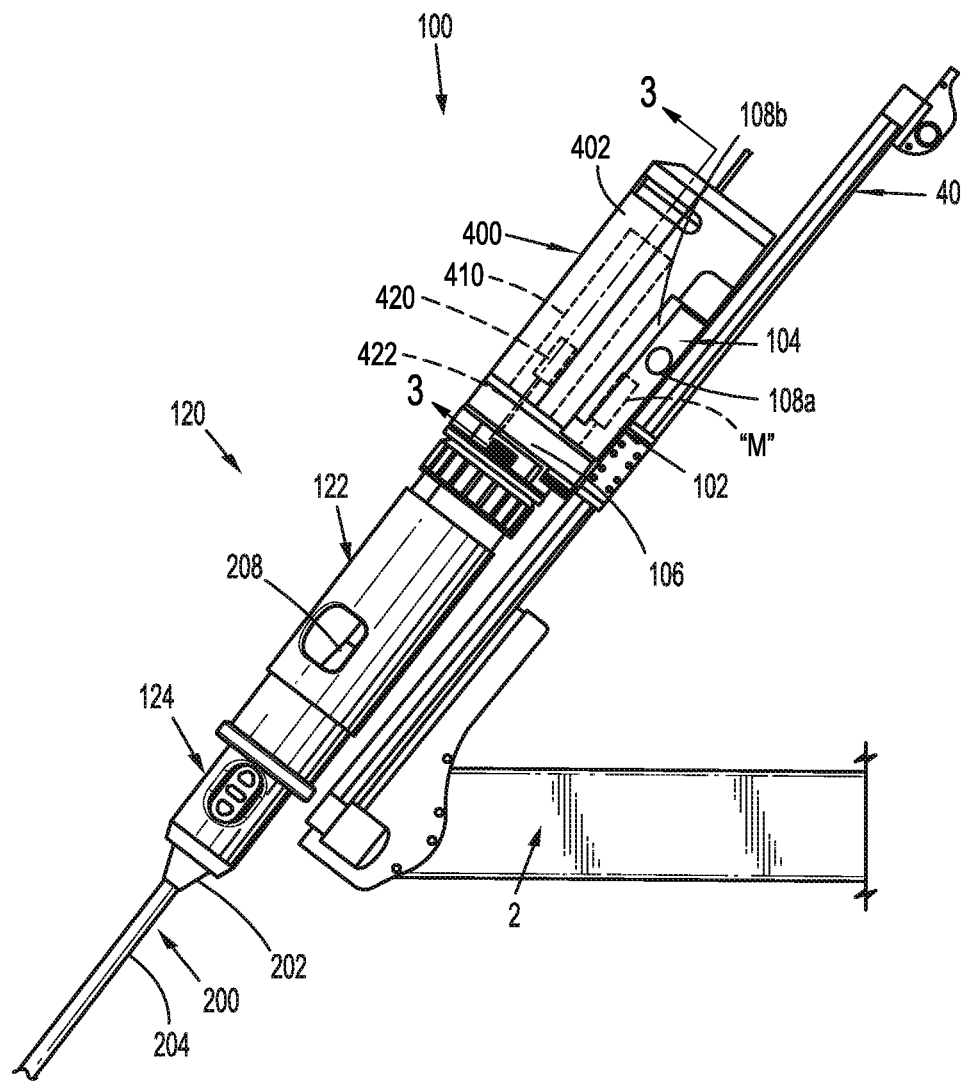
FIG. 2B is a side, perspective view of the surgical assembly of FIG. 1 including a surgical instrument holder, an IDU, an adapter assembly, and an endoscope.

With reference to FIGS. 1, 2A, and 2B, robotic surgical system 1 includes the robotic surgical assembly 100, which is coupled with or to robotic arm 2 or 3. The robotic surgical assembly 100 includes the surgical instrument holder 102, the IDU 400, the adapter assembly 120, and the surgical instrument 200A or endoscope 200B. IDU 400 transfers power and actuation forces from a motor 420 thereof to a drive assembly (not explicitly shown) of adapter assembly 120 to drive a rotation of surgical instrument 200A or endoscope 200B up to least about 180 degrees about its longitudinal axis "X." surgical instrument 200A or endoscope 200B may be rotated at least an additional 180 degrees by actuation of motor "M" supported in surgical instrument holder 102, which transfers its rotational motion to adapter assembly 120 and in turn to surgical instrument 200A or endoscope 200B. As such, surgical assembly 100 provides two mechanical pathways to adjust the rotational position of surgical instrument 200A or endoscope 200B, with each mechanical pathway resulting in a different rate of rotation of surgical instrument 200A or endoscope 200B, as will be described below.

With reference to FIG. 2B, surgical instrument holder 102 of surgical assembly 100 functions to support IDU 400 and to actuate a rotation of motor assembly 410 of IDU 400. Surgical instrument holder 102 includes a back member or carriage 104, and an outer member or housing 106 extending laterally (e.g., perpendicularly) from an end of carriage 104. In some embodiments, housing 106 may extend at various angles relative to carriage 104 and from various portions of carriage 104. Carriage 104 has a first side 108a and a second side 108b, opposite first side 108a. First side 108a of carriage 104 may be selectively connectable, or permanently connected to rail 40 of robotic arm 2, it is further contemplated that carriage 104 may only be removed from rail 40 of robotic arm 2 by a field technician or the like for maintenance or repair purposes. Surgical instrument holder 102 slides or translates along rail 40 of robotic arm 2. Second side 108b of carriage 104 is configured to non-rotatably support a housing or outer shell 402 of IDU 400.

Carriage 104 of surgical instrument holder 102 supports or houses a motor, such as, for example, canister motor "M" therein. Motor "M" receives controls and power from control device 4 to ultimately rotate internal motor assembly 410 of IDU 400. In some embodiments, carriage 104 may include a printed circuit board (not shown) in electrical communication with motor "M" to control an operation of motor "M" of carriage 104. Carriage 104 has a rotatable drive shaft (not shown) extending from motor "M" and longitudinally through carriage 104. The drive shaft of carriage 104 has a gear or coupling member (not shown) configured for operable engagement with a gear or coupling member (not shown) of motor assembly 410 of IDU 400 to transfer a rotation from motor "M" of surgical instrument holder 102 to motor assembly 410 of IDU 400, as will be described in detail below. In some embodiments, motor "M" of surgical instrument holder 102 may drive the rotation of motor assembly 410 of IDU 400 by any suitable drive mechanism, for example, a gear assembly, a rack and pinion, pulley friction drive, hydraulics, pneumatics, a cable, belt, or the like.

Housing 106 of surgical instrument holder 102 defines a channel (not shown) therethrough configured to rotatably receive and support IDU 400 therein. Housing 106 has a generally oblong semicircular shape, but in some embodiments, housing 106 may assume a variety of shapes, such as, for example, C-shaped, U-shaped, V-shaped, hook-shaped, or the like.

With continued reference to FIG. 2B, IDU 400 of surgical assembly 100 includes an outer housing 402 and an inner housing or motor assembly 410 rotatably disposed within outer housing 402. Outer housing 402 is engaged to second side 108b of carriage 104 of surgical instrument holder 102 and houses various components of IDU 400 as described in greater detail below. In some embodiments, outer housing 402 may be permanently or removably attached to second side 108b of carriage 104. Outer housing 402 of IDU 400 has a generally rectangular configuration, but in some embodiments, outer housing 402 may assume a variety of configurations, such as, for example, cylindrical, squared, elongate, tubular, or the like.

Outer housing 402 of IDU 400 may be configured and dimensioned to slidably receive motor assembly 410, a motor pack or the like therein. It is contemplated that the motor assembly 410 may be non-removable from the IDU 400. Upon coupling IDU 400 to surgical instrument holder 102, a drive assembly (not shown) of surgical instrument holder 102 operably engages motor assembly 410 of IDU 400 such that actuation of motor "M" of surgical instrument holder 102 effects a rotation of motor assembly 410 within outer housing 402 of IDU 400. For example, it is contemplated that the gear of drive shaft (not shown) extending from motor "M" of surgical instrument holder 102 is in operable engagement with a toothed inner or outer surface (not shown) of motor assembly 410 such that rotation of the gear attached to motor "M" of surgical instrument holder 102 rotates motor assembly 410. In some embodiments, surgical instrument holder 102 may have a pulley system that transfers rotational forces output by motor "M" of surgical instrument holder 102 into rotation of motor assembly 410. It is envisioned that any suitable mechanism may be provided to transfer the rotational forces output by motor "M" of surgical instrument holder 102 into a rotation of motor assembly 410.

Figure 3:
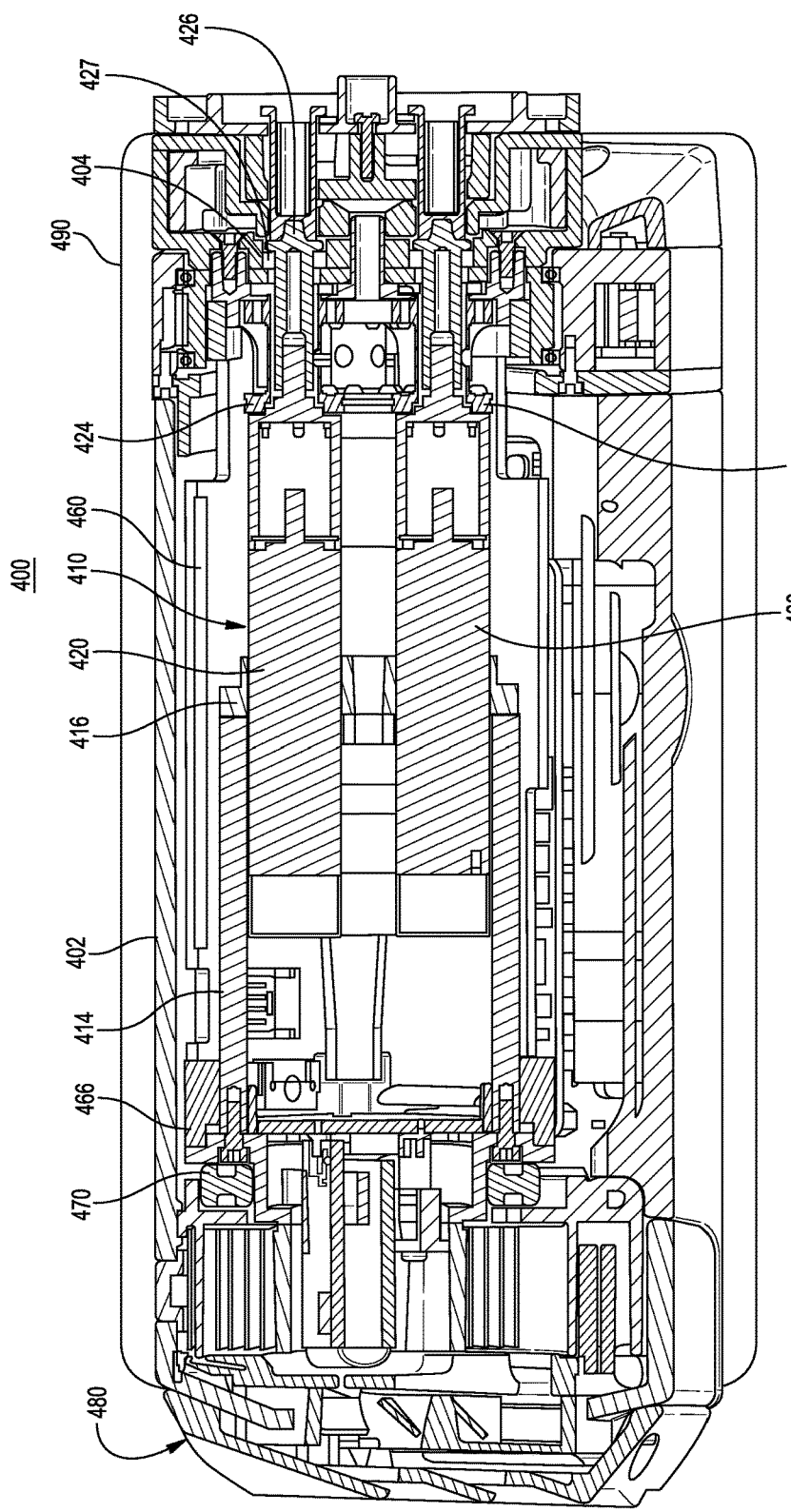
FIG. 3 is a cross-sectional view of the instrument drive unit of FIG. 2 taken along section line 3-3 of FIG. 2.
Figure 4:
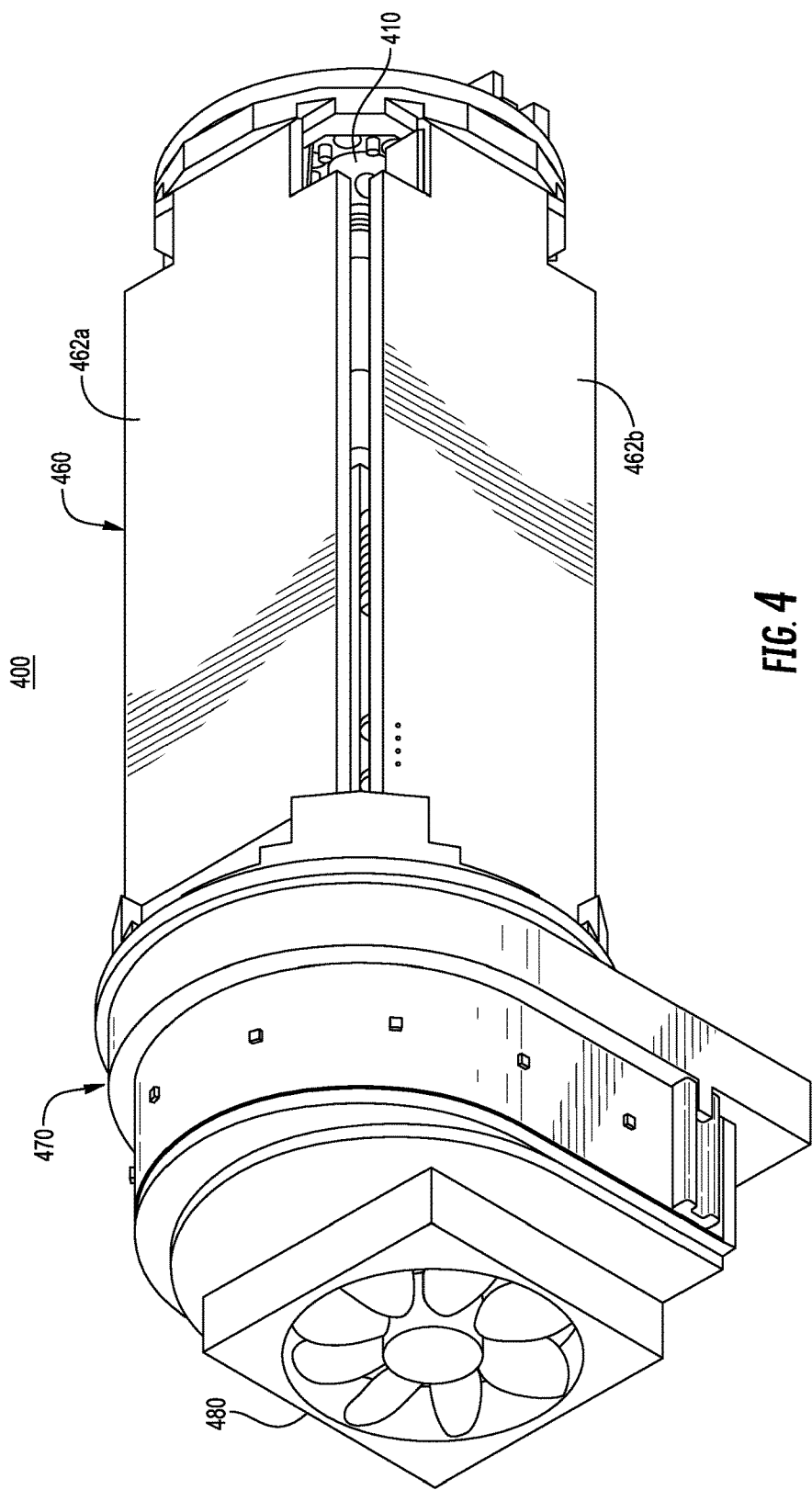
FIG. 4 is a perspective view of the instrument drive unit of FIG. 2 with the housing removed.
Figure 5:
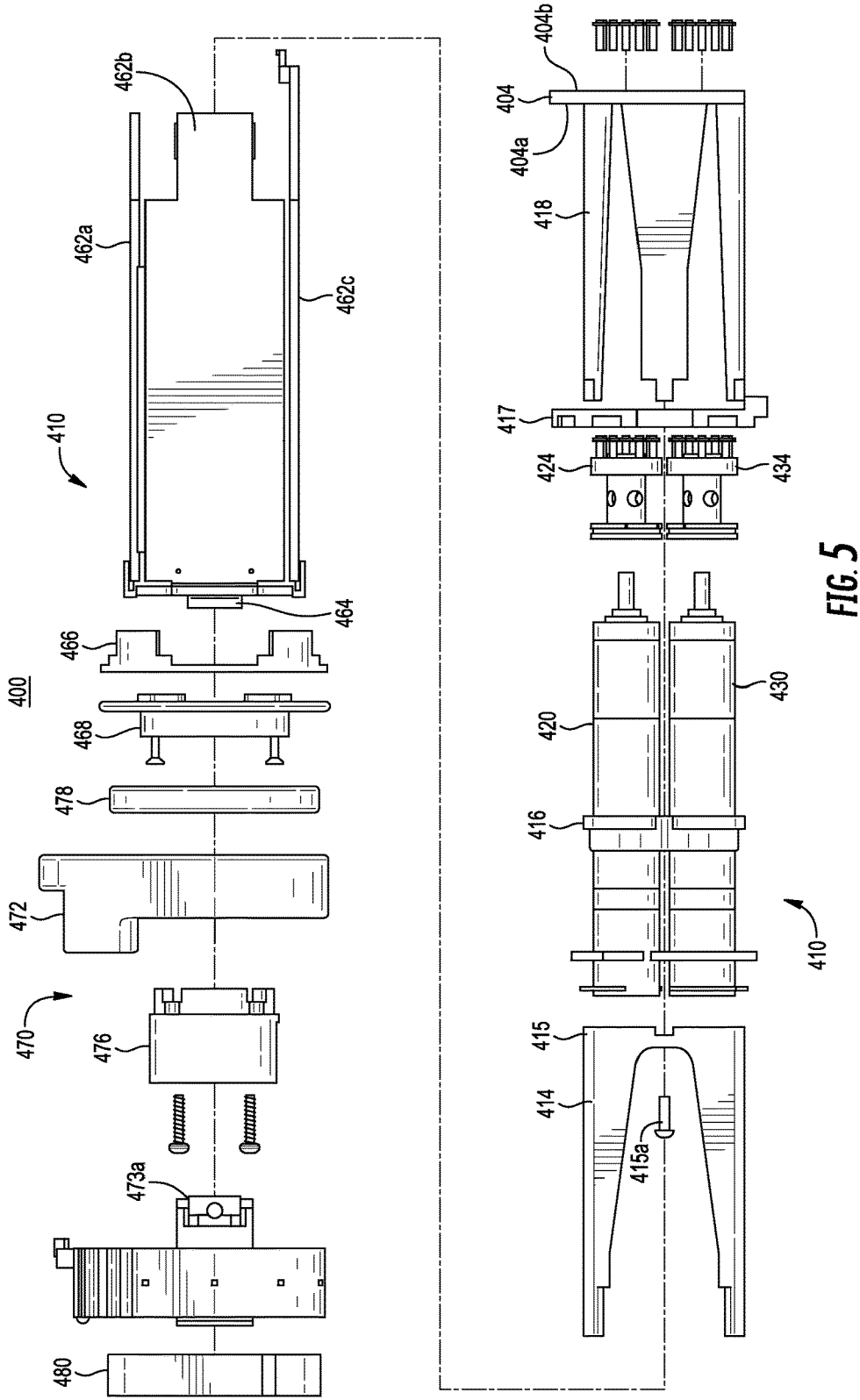
FIG. 5 is an exploded view of components of the instrument drive unit of FIG. 4.

With additional reference to FIG. 3, the motor assembly 410 may include four motors 420, 430, 440, 450 each having a drive shaft 422, 432, 442, 452 having a non-circular transverse cross-sectional profile (e.g., substantially D-shaped, or the like). In some embodiments, the drive shaft may have a circular transverse cross-sectional profile. The four motors 420, 430, 440, 450 are arranged in a rectangular formation such that respective drive shafts 422, 432, 442, 452 thereof are all parallel to one another and all extending in a common direction. A drive shaft 422 of the motor 420 of motor assembly 410 has a drive coupler, such as, for example, a crown gear 424 configured to operably couple to drive assembly (not explicitly shown) of adapter assembly 120. As motor 420 of motor assembly 410 is actuated, rotation of drive shaft 422 of motor 420 is transferred to drive assembly 160 of adapter assembly 120 to ultimately rotate endoscope 200 about its longitudinal axis "X."

For a detailed discussion of the construction and operation of an exemplary endoscope, reference may be made to U.S. patent application Ser. No. 62/615,677, filed Jan. 10, 2018, entitled "ROBOTIC SURGICAL ASSEMBLIES AND ADAPTER ASSEMBLIES THEREOF," the entire contents of which are incorporated by reference herein.

Referring to FIGS. 3-6, the IDU 400 is described in detail in accordance with the present disclosure. The IDU 400 includes an outer housing 402, a motor assembly 410, a control assembly 460, a rotation assembly 470, and a cooling unit 480. The IDU 400 can be covered by sterile covering or drape 490 to prevent contamination of the IDU 400 during a surgical procedure. The motor assembly 410 and the control assembly 460 may be integrated within a housing which will be covered by the drape 490 and will only be exposed to wipe down cleanings without being required to be exposed to autoclave sterilization or be exposed to submersion or automated washers. It is contemplated that the housing may be sealed or unsealed. The entire IDU 400 or portions of the IDU 400 including the motor assembly 410 and/or the control assembly 460 may be configured to have an operating temperature in a range of about 10° C. to about 65° C. and be capable of being stored in a temperature range of about −10° C. to about 55° C. The entire IDU 400 or portions of the IDU 400 including the motor assembly 410 and/or the control assembly 460 may be configured to operate and be stored in a relative humidity range of about 10% to about 85% and in an atmospheric pressure in a range of about 70 kPA to about 110 kPA.

As detailed below, the rotation assembly 470 is configured to limit rotation of the motor assembly 410 and the control assembly 460 about a longitudinal axis of the IDU 400 within the outer housing 402.

The motor assembly 410 is configured to engage the adapter assembly 120 (FIG. 2B) to control various aspects of a surgical instrument (e.g., endoscope 200B). The motor assembly 410 includes a proximal cage 414, a central isolator 416, a distal isolator 417, a distal cage 418, motors 420, 430, 440, 450, and torque transducers 424, 434, 444, 454. The distal cage 418 includes the mounting plate 404 of the IDU 400 that is coupled on a distal face 404b thereof to the proximal housing 122 of the adapter assembly 120 as detailed above. Each of the motors 420, 430, 440, 450 is secured within the motor assembly 410 in a manner which substantially isolates the motors 420, 430, 440, 450 from external forces other than torque generated by the respective motor 420, 430, 440, 450.

As detailed below, each of the torque transducers 424, 434, 444, 454 is configured to mount a respective motor to the mounting plate 404 in a structurally robust manner. The design of the torque transducers 424, 434, 444, 454 may also minimize the effects of the mass and inertia of the motor and minimize or eliminate the torsional and/or axial strain with the other transducers in the IDU 400. Further, each of the torque transducers 424, 434, 444, 454 is configured to provide accurate and repeatable torque readings when exposed to extreme operating temperatures and under heavy load cycling. In addition, each of the torque transducers 424, 434, 444, 454 is designed to degrade and/or fatigue in a consistent manner per cycle and/or over time when exposed to temperature extremes.

Figure 8:
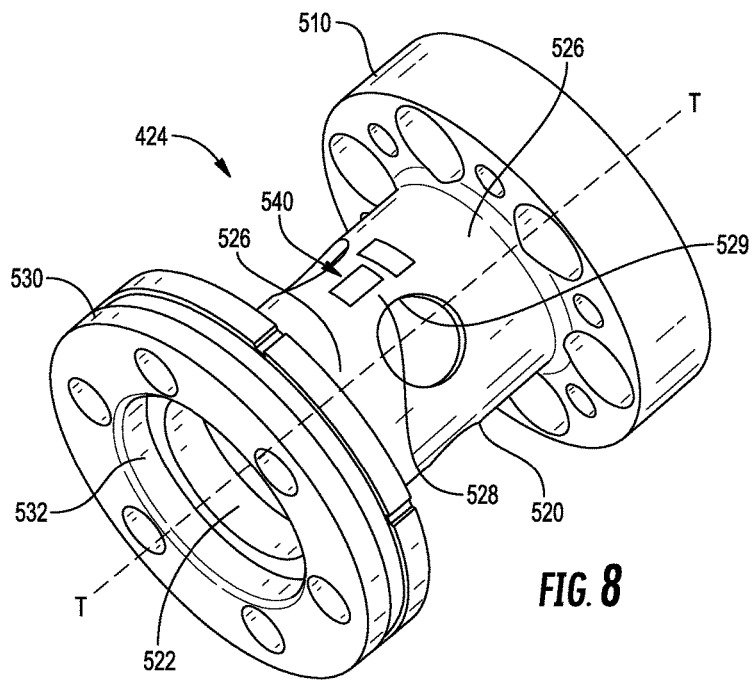
FIG. 8 is a rear perspective view of the torque transducer of FIG. 5.
Figure 9:
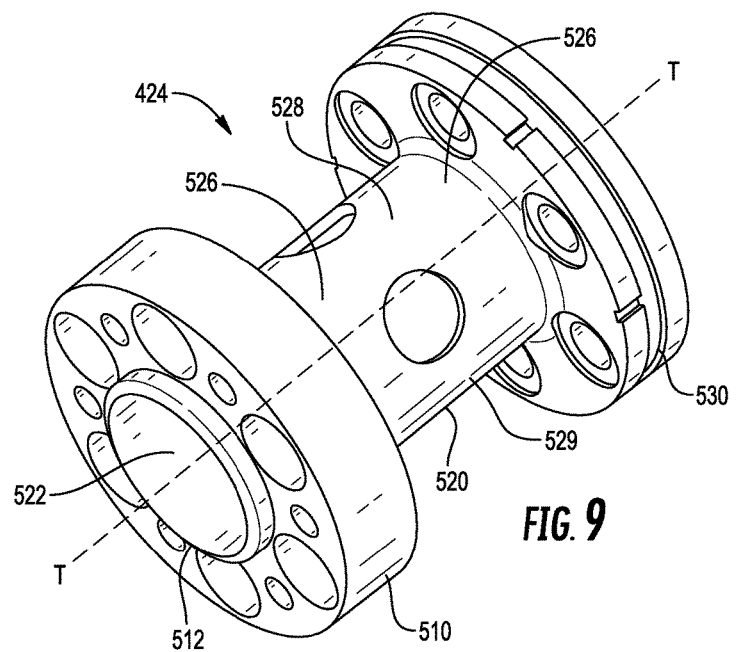
FIG. 9 is a front perspective view of the torque transducer of FIG. 5.
Figure 10:
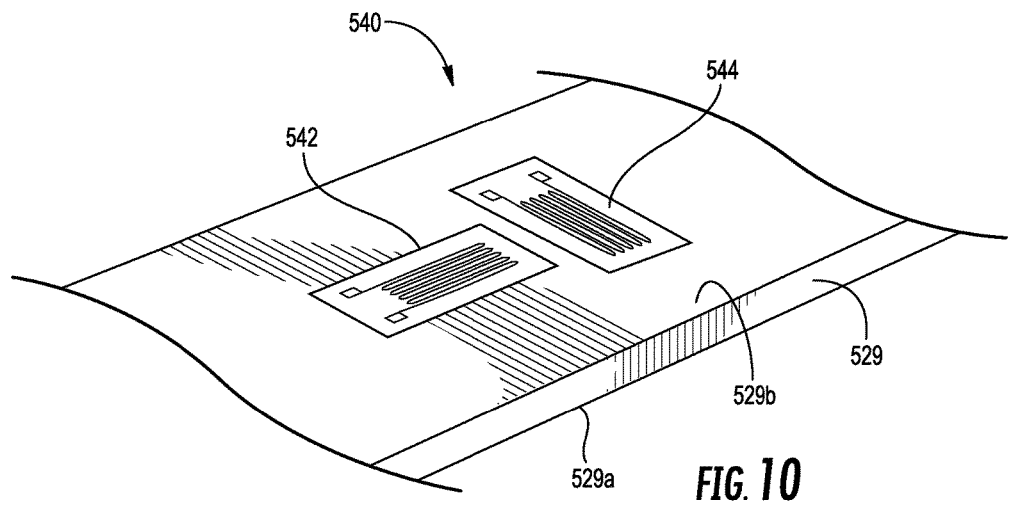
FIG. 10 is a schematic view of a strain gauge on the torque transducer of FIG. 8.

With additional reference to FIGS. 7-9, the mounting of motor 420 to the torque transducer 424 to secure the motor 420 within the motor assembly 410 is described in detail. It will be appreciated that each of the other motors 430, 440, 450 is mounted within the motor assembly 410 with a respective one of the torque transducer 434, 444, 454 in a similar manner. The torque transducers 424, 434, 444, 454 can be custom integrated torque sensors to provide flexibility in both packaging and tuning of design parameters to achieve a designed output response. It is envisioned that there may be cost advantages in utilizing such an integrated torque sensor. It is contemplated that these torque sensors can be specifically tuned for a specific application without a significant increase in cost. The design of the torque transducers 424, 434, 444, 454 can allow for tighter packing or reducing the size of the torque transducers 424, 434, 444, 454 when compared to a traditional torque transducer. As detailed herein below, the architecture of the torque transducers 424, 434, 444, 454 minimizes dynamic and static influences of motor mass, inertia, and weight on torque measured by the torque transducers 424, 434, 444, 454.

The torque transducer 424 includes a mounting flange 510, a motor flange 530, and a body 520 therebetween. The mounting flange 510 is coupled to a proximal face 404a of the mounting plate 404. The mounting flange 510 includes a locating feature or ring 512 that extends distally past the proximal face 404a of the mounting plate 404 to position or locate the torque transducer 424 relative to the mounting plate 404. The mounting flange 510 is secured to the mounting plate 404 by a plurality of fasteners 405a. The locating feature or ring 512 can allow for high clearance and tolerances for the fasteners 405a. The motor flange 530 is coupled to a distal portion of the motor 420 to secure the motor 520 within the motor assembly 410. The motor flange 530 is secured to the motor 420 by a plurality of fasteners 405b. The motor flange 530 can define a locating feature or recess 532 that receives a distal portion of the motor 420 to position or locate the motor 420 relative to the motor flange 530. The body 520 of the torque transducer 424 defines a channel 522 about a central longitudinal axis of the body 520 and includes a sensor assembly 524 for determining torque of the motor 420 as described in greater detail below. The motor 420 includes a drive shaft 422 that extends proximally from the motor 420, through the channel 522 of the torque transducer 424, and the mounting plate 404. The drive shaft 422 can include a drive coupler or gear 426 that engages the input 164 of the drive assembly 160 of the adapter assembly 120 as detailed above. A bearing 427 (FIG. 3) may be disposed between the drive coupler 426 and the front plate 404 to position the drive coupler 426 relative to the front plate 404.

During assembly with the motors 420, 430, 440, 450 coupled to the mounting plate 404, the central isolator 416 is disposed about a central portion of each of the motors 420, 430, 440, 450 to space the motors 420, 430, 440, 450 relative to one another while permitting each of the motors 420, 430, 440, 450 to rotate about an axis defined by the drive shaft 422, 432, 442, 452 of the respective motor 420, 430, 440, 450. The proximal cage 414 is positioned over the motors 420, 430, 440, 450 until a distal flange 415 of the proximal cage 414 abuts the central isolator 416. A fastener 415a passes through the distal flange 415, the central isolator 416, and into the distal cage 418 to secure the proximal cage 414 to the distal cage 418 with the central isolator 416 therebetween.

The control assembly 460 is disposed about the motor assembly 410. The control assembly 460 includes control boards 462a-d, a proximal isolator 466, and a retention plate 468. The control boards 462a-d are positioned along the sides of the motor assembly 410 disposed along the sides of the proximal and distal cages 414, 418. The each of the control boards 462a-d is electrically coupled to one or more of the motors 420, 430, 440, 450 to actuate or rotate the motors 420, 430, 440, 450 in response to control signals. The control boards 462a-d are each electrically coupled to a connector 464 to receive control signals from the control device 4 (FIG. 1). The retention plate 468 is coupled to the proximal cage 414 of the motor assembly 410 to secure the control boards 462a-d to the motor assembly 410 with the proximal isolator 466 disposed between the retention plate 468 and the control assembly 460. The control assembly 460 may be secured by being "sandwiched" between distal isolator 417 and proximal isolator 466. Positioning the control boards 462a-d adjacent the torque transducers 424, 434, 444, 454 may make the torque transducers 424, 434, 444, 454 less susceptible to electromagnetic and radiofrequency induced noise as a result of reduced or shorter cable requirements. It is contemplated that the connector 464 can be used to test, calibrate, and qualify the final IDU assembly.

The rotation assembly 470 includes a spool plate 472, an inner cup 476, and a rotation limiter 478. The spool plate 472 is disposed about the rotation limiter 478 which is disposed about the retention plate 468 to limit the rotation of the IDU 400. The inner cup 476 engages the retention plate 468, and thus the motor assembly 410, to rotate the motor assembly 410 about the central axis of the IDU 400. The spool plate 472 includes an internal connector 473a that couples to the connector 464 of the control assembly 460 to transmit control signals to the motors 420, 430, 440, 450. The proximal spool plate 472 also includes an external connector 473b that receives control signals from the control device 4 and is electrically coupled to the motors 420, 430, 440, 450 via the control boards 462a-d.

The cooling unit 480 is mounted to the spool plate 472 and is configured to circulate cooling fluid through the IDU 400 to cool internal mechanical components (e.g., motors 420, 430, 440, 450) and internal electrical components (e.g., circuit boards 162a-d). The cooling unit 480 can include a fan that draws air from within the IDU 400 or forces air through the IDU 400.

For additional detail of the control assembly 460, rotation assembly 470, and cooling unit 480 reference can be made to U.S. Provisional Patent Application Ser. No. 62/341,714, filed May 26, 2016 (now PCT Application No.: PCT/US17/33899, filed on May 23, 2017), and entitled "ROBOTIC SURGICAL ASSEMBLIES," the entire contents of which are hereby incorporated by reference.

As detailed above, the torque transducer 424 is configured as a reaction torque sensor to provide improved precise real-time measurements of torque delivered by the motor 420 when compared to tradition torque sensors. Traditional torque sensors measure the torque delivered by a motor (e.g., motor 420) by measuring the current delivered to the motor to rotate the motor at a given speed and calculating the torque from known values. Thus, traditional torques sensors require a motor to be energized (e.g., current to be delivered to the motor) to measure the torque of the motor whereas, the torque transducer 424 is capable of measuring torque of the motor 420 when the motor 420 is energized or denergized. It will be appreciated that the IDU 400 can include traditional torque sensors to verify torque measurements of the torque transducer 424 are within an expected range or to act as a safety shut off in case of unexpected readings from the torque transducer 424. Examples of traditional torque sensors being used in conjunction with reaction torque sensors are disclosed in International Patent Application PCT/US16/37478, filed Jun. 15, 2016, entitled "ROBOTIC SURGICAL SYSTEM TORQUE TRANSDUCTION SENSING," the entire contents of which are hereby incorporated by reference.

By integrating the torque transducer 424 into the IDU 400, torque of the motor 420 is directly measured which can reduce noise in the measured torque when compared to traditional torque measurements. For example, the torque transducer detailed herein have been shown to have a repeatable accuracy of ±2 mNM. In addition, mounting the torque transducer 424 at the distal end of the motor 420 and over the drive shaft 422 can provide an additional reduction of noise in the measured torque. Further, the configuration of torque transducer 424, as detailed herein, allows for sampling of torque measurements at a rate of about 10 KHz to about 50 KHz (e.g., about 0.000008 seconds to about 0.00004 seconds) compared to about 50 to about 100 Hz (e.g., about 0.01 to about 0.05 seconds) for traditional torque measurements. The increased sampling rate can allow for faster dynamic response rates to changes in the torque of the motor 420. The increased sampling rate can provide increased accuracy in real time feedback (e.g., visual, audible, or haptic feedback) to a clinician controlling the IDU 40.

By allowing faster dynamic response rates, precision in the management of drive torques of each motor (e.g., motor 420, 430, 440, 450) of IDU 400 can be increased. This increased precision translates to more precise control parameters of surgical instruments driven by the IDU 400 including, but not limited to, cable tensions, rod tensions, and angular rotations of shafts. The increased precision can mitigate damage from loads that will increase the usable life and reliability of the surgical instruments. In addition, the increase precision can increase the accuracy of the torsional forces which allows for simplified calibrations and setting of limits for hard stops and bindings for drives and cables. Further, the increased precision can be used to monitor cable displacement versus load parameters to detect fatigue, stretching, or degradation to monitor end of life of drive cables.

Referring to FIGS. 8-11, the torque transducer 424 is configured as a reaction torque transducer to measure torque of the motor 420. As detailed above, the torque transducer 424 includes the mounting flange 510, the body 520, and the motor flange 530. The body 520 is generally cylindrical and defines a central longitudinal or transducer axis T-T and defines the channel 522 about the transducer axis T-T. The mounting and motor flanges 510, 530 are constructed to minimize or prevent torsional deflection about the transducer axis T-T. In addition, the mounting flange 510 is secured to the mounting plate 404 by a plurality of fasteners and the motor flange 530 is secured to the distal end portion of the motor 420 to minimize or prevent torsional deflection. The mounting flange 510 and/or the motor flange 530 may be secured to the mounting plate 404 and the motor 420, respectively.

The body 520 is configured to twist or deflect in response to torque of the motor 420. The body 520 can include low strain regions 526 and high strain regions 528 interconnecting the mounting and motor flanges 510, 530. The low strain regions 526 are contiguous ring about the transducer axis T-T and the high strain regions 528 define openings or gaps about the transducer axis T-T such that the high strain regions 528 have increased deflection (e.g., experience additional strain) when compared to the low strain regions 526 in response to the same torque of motor 420. In addition, the openings or gaps can allow access to a driver to engage the fasteners 405a, 405b to secure the torque transducer 424. It is contemplated that the high strain regions 528 can be contiguous rings constructed of a different material or having different material properties from the low strain regions 526 such that the high strain regions 528 have increased deflection in response to torque when compared to the low strain regions 526. The high strain region 528 may be in in the form of a strut 529 that extends between the mounting and motor flanges 510, 530.

The torque transducer 424 includes a strain gauge 540 disposed on or in the high strain region 528. The strain gauge 540 can be disposed on an inner surface 529a or an outer surface 529b of the high strain region 528 or can be etched into the high strain region 528. The strain gauge 540 is positioned on a portion of the high strain region 528 subject to a maximum flexation or deflection as torque is applied to the torque transducer 424. The strain gauge 540 includes an active strain sensor 542 and a calibration strain sensor 544. The active strain sensor 542 is orientated to measure deflection or flex of the high strain region 528 in response to torque being applied to the torque transducer 424 about the transducer axis T-T as such the active strain sensor 542 measures radial strain of the high strain region 528. The calibration strain sensor 544 is aligned perpendicular to the active strain sensor 542 such that the calibration strain sensor 544 is subject to little or no radial deflection of the high strain region 528 about the transducer axis T-T. The calibration strain sensor 544 measures strain of the high strain region 528 in response to factors other than radial deflection (e.g., thermal expansion of the body 520). It is contemplated that the calibration strain sensor 544 can be used to detect axial tension or compressive forces. In addition, the calibration strain sensor 544 can be used to monitor for improper usage, linear drive thrust loads, and/or strain loading conditions of the couplers 206, 208. Further, the strain gauge 540 can include integrated electronics (e.g., EEPROM or microprocessors) to monitor life, gauge, cold starts, load limits, serialization, thermal limits, and calibration offsets that can be read and used to optimize and control the life of the strain gauge 540.

Figure 11:
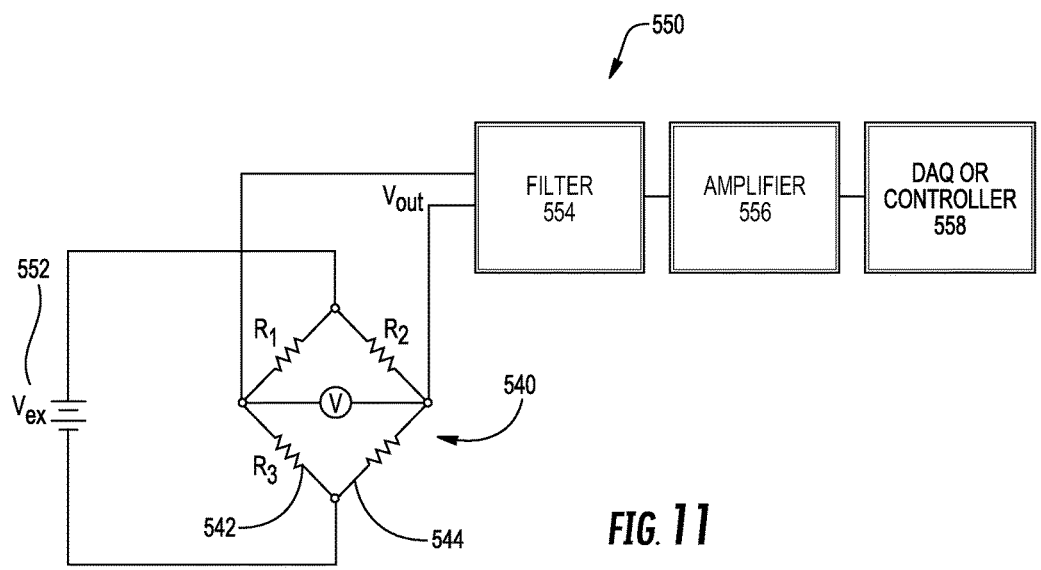
FIG. 11 is a schematic view of a sensor circuit of the strain gauge of FIG. 8.

With particular reference to FIG. 11, a measurement circuit 550 determines the reaction torque of the motor 420 from the strain measured by the strain gauge 540. The measurement circuit 550 includes the strain gauge 540, a voltage source 552, a filter 554, an amplifier 556, and a controller 558. The strain gauge 540 includes the active strain sensor 542 and the calibration strain sensor 544 as part of a bridge circuit including two resistors $R_1$, $R_2$. Strain of the body 520 of the torque transducer 424 is measured as a voltage change of the strain gauge 440 whereby the resistance of each of the strain sensors 542, 544 varies in response to flexation of the body 520. The measured voltage is passed from strain gauge 540 to a filter 554. As shown, the measured voltage accounts for factors other than the flexation of the body 520 as a result of positioning the calibration strain sensor 544 adjacent and aligned orthogonal to the active strain sensor 542. The filter 554 is a low pass filter to remove noise from the measured voltage. The filter 554 transmits the filtered voltage to an amplifier 556 which transmits the amplified voltage to a controller 558. The controller 558 detects changes in the amplified voltage and calculates a strain of the body 520 of the torque transducer 424. From the strain of the body 520 of the torque transducer 424, the controller 558 calculates the flexation of the body 520. The controller 558 calculates reaction torque of the motor 420 from the flexation of the body 520 of the torque transducer 424 in view of the known properties and dimensions of the body 520. The controller 558 transmits the calculated reaction torque of the motor 420 to the control device 4 (FIG. 1). The sampling rate of the measurement circuit 550 may be greater than about 3 kHz.

The control device 4 analyzes the reaction torque of the motor 420 to determine the force applied to the adapter 160 by the IDU 60. The control device 4 may adjust energy supplied to the motor 420 in response to the force applied to the end effector 20. Additionally or alternatively, the control device 4 may provide feedback to a user through the operating console 5 in response to the reaction torque of the motor 420. The feedback may be visual, audible, or haptic.

The strain gauge 540 includes leads (not explicitly shown) that extend to the measurement circuit 550. The body 520 can include a snap or epoxy to secure the leads to the body 520 and provide strain relief for the leads.

Figure 12:
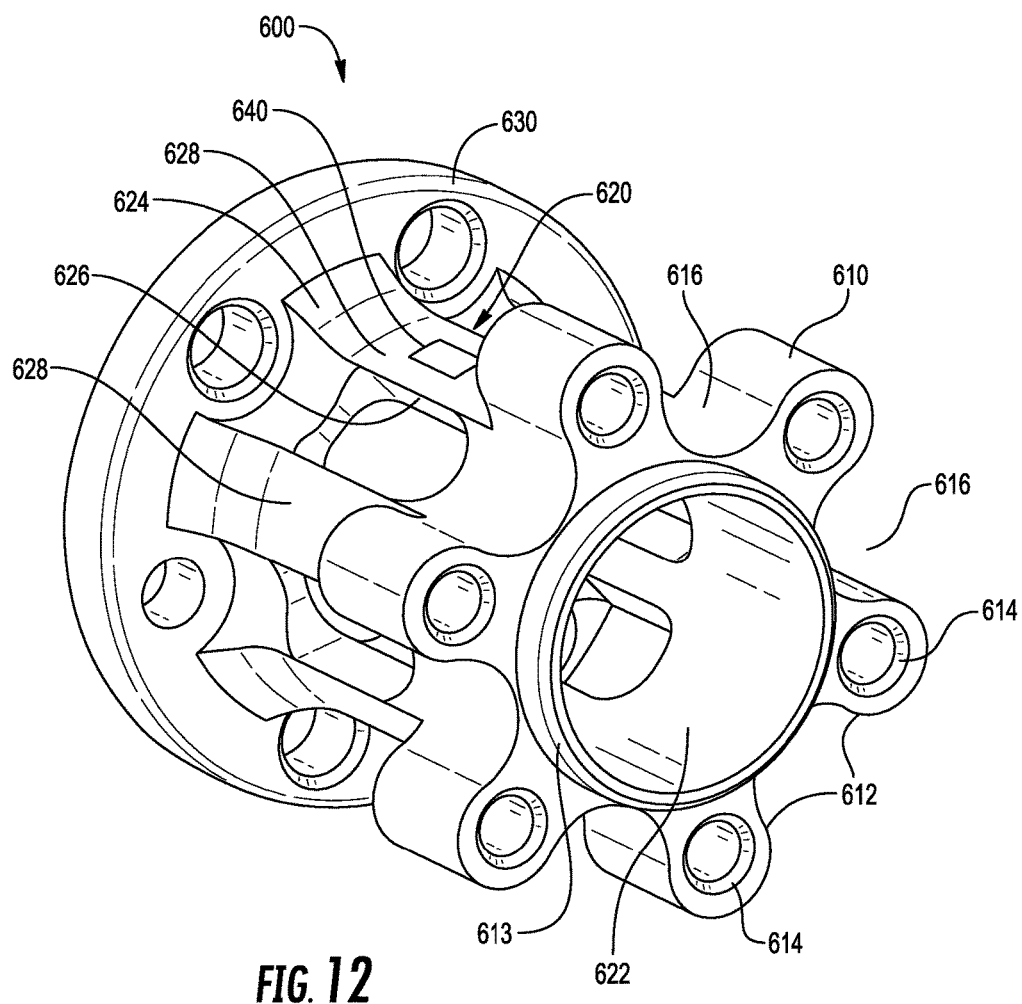
FIG. 12 is another torque transducer provided in accordance with the present disclosure.

Referring now to FIG. 12, another torque transducer 600 is disclosed in accordance with the present disclosure. The torque transducer 600 includes a mounting flange 610, a motor flange 630 and a body 620 interconnecting the mounting and motor flanges 610, 630. The mounting flange 610 is formed from a ring of radial protrusions 613 that each define a fastener hole 614 for receiving a fastener to secure the mounting flange 610 to a fixed plate (e.g., mounting plate 404). The mounting flange 610 defines recesses 616 between each of the radial protrusions 613. The recesses 616 may be used to route wiring to the strain gauge 640 or between the IDU 400 and the adapter 120. Additionally or alternatively, the recesses 616 may provide driver access to the fasteners of the motor flange 630. The mounting flange 610 may include a locating feature or ring 612 that extends distally to position or locate the torque transducer 600 relative to the mounting plate 404. The motor flange 630 is substantially similar to the motor flange 530 detailed above and will not be discussed further for reasons of brevity.

The body 620 is similar to the body 520 of torque transducer 424 detailed above, as such only differences will be detailed herein. The body 620 is generally cylindrical and formed from a plurality of struts 628 that extend between the mounting and motor flanges 610, 630 to define a channel 622 through the body 620. The struts 628 are configured to deflect or flex in response to torque applied about the transducer axis T-T. The struts include a low stress regions 624 adjacent each of the mounting and motor flanges 610, 630 and a high stress region 626 between the low stress sections 626. The body 620 includes a stress gauge 640 disposed in the high stress region of at least one of the struts 628. The stress gauge 640 is similar to the stress gauge 540 detailed above.

The weight of the body 520, 620 may be minimized while having dimensions suitable for mounting the motors 420, 430, 440, 450 within the IDU 400 and being capable of withstanding the operating torques of the motors 420, 430, 440, 450 without permanent deformations of the body 520, 620. In some applications, each of the torque transducers 424, 434, 444, 454, 600 may have a light use torque range of about ±14 mNm and a heavy use torque range of about ±350 mNm both with a high resolution of accuracy. In particular applications, the anticipated peak torque of each of the torque transducers 424, 434, 444, 454, 600 may be about ±700 mNm such that the torque transducer 424, 434, 444, 454, 600 may be designed to withstand a momentary torque of about ±1400 mNm without permanent deformations of the body 520, 620 which may produce a lower resolution of accuracy. In certain applications, the body 520, 620 may be configured to withstand ±22 N of axial loading without experiencing plastic deformation. The duty cycle of the torque transducer 424, 434, 444, 454, 600 may be rated at 100% for light use, 50% for heavy use, and less than 5% at or near peak torque.

Using torque transducer 600 as an example, the outer diameter of the body 620 may be less than about 17.5 mm, e.g., about 9.5 mm, and the mounting and motor flanges 610, 630 may have a diameter of less than about 22 mm, e.g., about 17 mm. The locating ring 612 may have an outer diameter of about 9 mm.

The torque transducers detailed herein (e.g., torque transducers 424, 434, 444, 454, 600) can be of a one piece design that utilize low fatigue life materials or alloys which can include, but are not limited to, steel, stainless steel, titanium, aluminum, or alloys thereof. Alternatively, the torque transducers detailed herein can be a multi-piece structure of one of the above materials or a combination thereof. For example, the torque transducers 424, 434, 444, 454, 600 may be constructed of 17-4 stainless steel and/or 2024-T351 aluminum. When a torque transducer 424, 434, 444, 454, 600 are constructed of an aluminum or an aluminum alloy, the torque transducer 424, 434, 444, 454, 600 may be anodized per a military specification, e.g., MIL-A-8625F Type II, class 1, or be coated with a protective coating, e.g., Alodine 5200 non-chrome conversion coating. It is also contemplated that the torque transducers 424, 434, 444, 454, 600 may be enhanced with a passivate treatment to improve rust and corrosion resistance.

It will be understood that various modifications may be made to the embodiments disclosed herein. Therefore, the above description should not be construed as limiting, but merely as exemplifications of various embodiments. Those skilled in the art will envision other modifications within the scope of the claims appended thereto.

What is claimed is:

1. A torque transducer for mounting a motor, comprising:
a mounting flange configured to secure the torque transducer to a fixed structure;
a motor flange configured to secure to a motor;
a body interconnecting the mounting and motor flanges, the body defining a channel about a longitudinal axis of the body, the body configured to flex in response to the mounting flange and the motor flange rotating relative to one another in response to torque of the motor; and
a strain gauge positioned on the body to measure flexation of the body.

2. The torque transducer according to claim 1, wherein the body has a high strain region configured to amplify flexation in response to a given torque.

3. The torque transducer according to claim 2, wherein the body has a low strain region adjacent each of the mounting and motor flanges, the high strain region disposed between the low strain regions.

4. The torque transducer according to claim 1, wherein the mounting flange includes a ring configured to position the torque transducer relative to a fixed structure.

5. The torque transducer according to claim 1, wherein the motor flange defines a recess configured to position the torque transducer relative to a motor.

6. An instrument drive unit comprising:
a mounting plate;
a first motor having a drive shaft extending towards the mounting plate; and
a first torque transducer securing the first motor to the mounting plate, the first torque transducer including:
a motor flange secured to the first motor;
a mounting flange secured to the mounting plate;
a body interconnecting the mounting and motor flanges, the body defining a channel about a longitudinal axis of the body, the body configured to flex in response to the mounting flange and the motor flange rotating relative to one another in response to torque of the first motor, the drive shaft of the first motor extending into the channel; and
a strain gauge positioned on the body to calculate torque applied by the first motor from flexation of the body.

7. The instrument drive unit according to claim 6, wherein the first torque transducer is configured to sample torque of the first motor at a rate in a range of about 10 KHz to about 50 KHz.

8. The instrument drive unit according to claim 6, wherein the first torque transducer is configured to measure torque of the first motor when the first motor is energized and when the first motor is deenergized.

9. The instrument drive unit according to claim 6, wherein the mounting flange includes a ring disposed about the channel and extending towards the mounting plate, the mounting plate receiving the ring to position the first torque transducer relative to the mounting plate.

10. The instrument drive unit according to claim 6, wherein the motor flange defines a recess about the channel, the first motor received in the recess to position the first motor relative to the first torque transducer.

11. The instrument drive unit according to claim 6, further comprising a motor assembly including:
the first motor;
a second motor secured to the mounting flange by a second torque transducer;
a third motor secured to the mounting flange by a third torque transducer; and
a fourth motor secured to the mounting flange by a fourth torque transducer.

12. The instrument drive unit according to claim 11, further comprising a cage assembly extending proximally from the mounting flange, the cage assembly disposed about the motor assembly, each of the motors of the motor assembly suspended within the motor assembly by a respective one of the torque transducers such that rotation of each motor about a respective longitudinal motor axis is unrestrained except for by a respective one of the torque transducers.

* * * * *